United States Patent
Taniike et al.

(10) Patent No.: US 6,885,196 B2
(45) Date of Patent: Apr. 26, 2005

(54) BIOSENSOR

(75) Inventors: Yuko Taniike, Osaka (JP); Shin Ikeda, Katano (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 17 days.

(21) Appl. No.: 10/220,153

(22) PCT Filed: Jul. 17, 2001

(86) PCT No.: PCT/JP01/06188
§ 371 (c)(1),
(2), (4) Date: Aug. 27, 2002

(87) PCT Pub. No.: WO02/08743

PCT Pub. Date: Jan. 31, 2002

(65) Prior Publication Data

US 2003/0032875 A1 Feb. 13, 2003

(30) Foreign Application Priority Data

Jul. 24, 2000 (JP) .................................... 2000-222266

(51) Int. Cl.[7] ................................................ A61B 5/05
(52) U.S. Cl. ..................... 324/444; 324/438; 324/449; 204/403.11; 204/403.14
(58) Field of Search ................................ 600/345, 347, 600/365, 364; 435/14; 422/68.1; 204/403, 403.11, 403.14; 324/438, 444, 449, 450, 452, 453, 464, 698

(56) References Cited

U.S. PATENT DOCUMENTS

| | | | | |
|---|---|---|---|---|
| 5,437,999 A | 8/1995 | Diebold et al. | ........ | 204/403.11 |
| 5,508,171 A * | 4/1996 | Walling et al. | .......... | 205/777.5 |
| 6,212,417 B1 | 4/2001 | Ikeda et al. | ............ | 204/403.14 |
| 6,413,410 B1 * | 7/2002 | Hodges et al. | ............... | 205/775 |

FOREIGN PATENT DOCUMENTS

| | | |
|---|---|---|
| EP | 0 685 737 A1 | 12/1995 |
| EP | 0 795 601 A2 | 9/1997 |
| EP | 0 964 059 A2 | 12/1999 |
| EP | 0 969 097 A2 | 1/2000 |
| EP | 0 969 282 A2 | 1/2000 |
| EP | 0 984 069 A2 | 3/2000 |
| JP | 3-202764 | 9/1991 |
| JP | 9-159642 | 6/1997 |
| JP | 10-2874 | 1/1998 |
| JP | 11-352093 | 12/1999 |
| JP | 2000-65777 | 3/2000 |
| JP | 2000-258382 | 9/2000 |
| WO | WO 91/09139 | 6/1991 |
| WO | WO 98/35225 | 8/1998 |

OTHER PUBLICATIONS

"Biosensor" ed. by Shuichi Suzuki, Kodansha pp 100–103, Mar. 10, 1984.

* cited by examiner

Primary Examiner—Vincent Q. Nguyen
(74) Attorney, Agent, or Firm—McDermott Will & Emery LLP

(57) ABSTRACT

A highly sensitive biosensor that uses a smaller amount of sample for measurement is described. The biosensor includes a first insulating base plate having a working electrode, a second insulating base plate having a counter electrode opposed to the working electrode, and a reagent layer containing at least an oxidoreductase. The biosensor further includes a sample supply pathway formed between the first and second insulating base plates, where the working electrode, counter electrode and reagent layer are exposed to an inside of the sample supply pathway, and the distance between the working electrode and the counter electrode is 150 μm or less.

6 Claims, 10 Drawing Sheets

Height of sample supply pathway (μm)

working electrode-counter electrode distance (μm)

BIOSENSOR

TECHNICAL FIELD

The present invention relates to a biosensor for rapid and highly accurate quantification of a substrate contained in a sample.

BACKGROUND ART

Methods using polarimetry, colorimetry, reductimetry and a variety of chromatographies have been developed as methods for quantitative analysis of sugars such as sucrose and glucose. These methods, however, are all poorly specific to sugars and hence have poor accuracy. Among these methods, the polarimetry is simple in manipulation, but is largely affected by the temperature during the manipulation. Therefore, the polarimetry is not suitable as a method for simple quantification of sugars at home, etc. for ordinary people.

Recently, various types of biosensors utilizing the specific catalytic action of enzymes have been under development.

The following will describe a method of glucose quantification as one example of the method of quantifying a substrate contained in a sample.

As an electrochemical method of glucose quantification, a method using glucose oxidase (EC 1.1.3.4: hereinafter abbreviated to GOD) as an enzyme and an oxygen electrode or a hydrogen peroxide electrode is generally well-known (see "Biosensor" ed. by Shuichi Suzuki, Kodansha, for example).

GOD selectively oxidizes β-D-glucose as a substrate to D-glucono-δ-lactone using oxygen as an electron mediator. In the presence of oxygen, oxygen is reduced to hydrogen peroxide during the oxidation reaction process by GOD. The decreased amount of oxygen is measured by the oxygen electrode, or the increased amount of hydrogen peroxide is measured by the hydrogen peroxide electrode. Since the decreased amount of oxygen and the increased amount of hydrogen peroxide are proportional to the content of glucose in the sample, glucose quantification is possible based on the decreased amount of oxygen or the increased amount of hydrogen peroxide.

The above method utilizes the specificity of the enzyme reaction to enable accurate quantification of glucose in the sample. However, as speculated from the reaction process, there is a drawback that the measurement results are largely affected by the oxygen concentration of the sample, and if the oxygen is absent in the sample, the measurement is infeasible.

Under such circumstances, glucose sensors of new type have been developed which use as the electron mediator potassium ferricyanide, an organic compound or a metal complex such as a ferrocene derivative and a quinone derivative without using oxygen as the electron mediator. In the sensors of this type, reduced form electron mediator resulting from the enzyme reaction is oxidized on a working electrode, and the concentration of glucose contained in the sample can be determined based on the amount of this oxidation current. At this time, on a counter electrode, a reaction in which oxidized form electron mediator is reduced to produce reduced form electron mediator proceeds. With the use of such an organic compound or metal complex as the electron mediator in place of oxygen, it is possible to form a reagent layer while a known amount of GOD and the electron mediator are carried in a stable state and a precise manner on the electrode, so that accurate quantification of glucose is possible without being affected by the oxygen concentration of the sample. It is also possible to integrate the reagent layer containing the enzyme and electron mediator, in an almost dry state, with an electrode system, and hence disposable glucose sensors based on this technique have recently been receiving a lot of attention. A typical example thereof is a biosensor disclosed in Japanese Patent Publication No. 2517153. In such a disposable glucose sensor, it is possible to measure glucose concentration easily with a measurement device by simply introducing a sample into the sensor connected detachably to the measurement device.

In the measurement made by such a glucose sensor, it is possible, with the use of a sample whose amount is in the order of several $\mu l$, to determine substrate concentration in the sample readily. However, in recent years, it is anxiously desired in various fields to develop biosensors that enable measurements with the use of a sample in a further smaller amount of about not more than 1 $\mu l$. The conventional electrochemical glucose sensors have an electrode system that is arranged on one plane in most cases. When the amount of sample is extremely small, such an arrangement increases the resistance to electric charge transfer between the electrodes, mainly ion transfer, possibly resulting in variations in measurement results.

Thus, there is proposed a biosensor having a working electrode and a counter electrode that are arranged so as to be opposed to each other (Japanese Laid-Open Patent Publication No. Hei 11-350293). In this type of sensor, the opposite arrangement of the working electrode and counter electrode facilitates ion transfer between the working electrode and the counter electrode, and for this reason and other reasons, this type of sensor is capable of quantifying a substrate such as glucose contained in a sample with higher accuracy and higher sensitivity than the conventional biosensors having an electrode system arranged on one plane.

Since it is requested recently to further reduce the amount of sample necessary for measurement, there is a need to realize a biosensor having a further higher sensitivity that enables measurements with the use of a further smaller amount of sample.

In view of the above problems, an object of the present invention is to provide a highly sensitive biosensor that needs a smaller amount of sample for measurement.

DISCLOSURE OF INVENTION

A biosensor of the present invention comprises a first insulating base plate having a working electrode, a second insulating base plate having a counter electrode opposed to the working electrode, a reagent layer comprising at least an oxidoreductase, and a sample supply pathway formed between the first and second insulating base plates, and is characterized in that the working electrode, counter electrode and reagent layer are exposed to an inside of the sample supply pathway and that the distance between the working electrode and the counter electrode is 150 $\mu m$ or less.

It is preferred that the area of a portion of the counter electrode exposed to the sample supply pathway be equal to or smaller than the area of a portion of the working electrode exposed to the sample supply pathway and that the counter electrode be positioned immediately above the working electrode.

The area $S_1$ of the portion of the working electrode exposed to the sample supply pathway is preferably 0.01 to 2.0 mm² and more preferably 0.1 to 2.0 mm², and the area $S_2$ of the portion of the counter electrode exposed to the sample supply pathway is preferably 0.005 to 20 mm² and more preferably 0.05 to 2.0 mm², and it is preferred that $S_2 \leq S_1$.

An arrangement of interposing a spacer member between the first and second base plates is preferred.

BEST MODE FOR CARRYING OUT THE INVENTION

Figure 1:
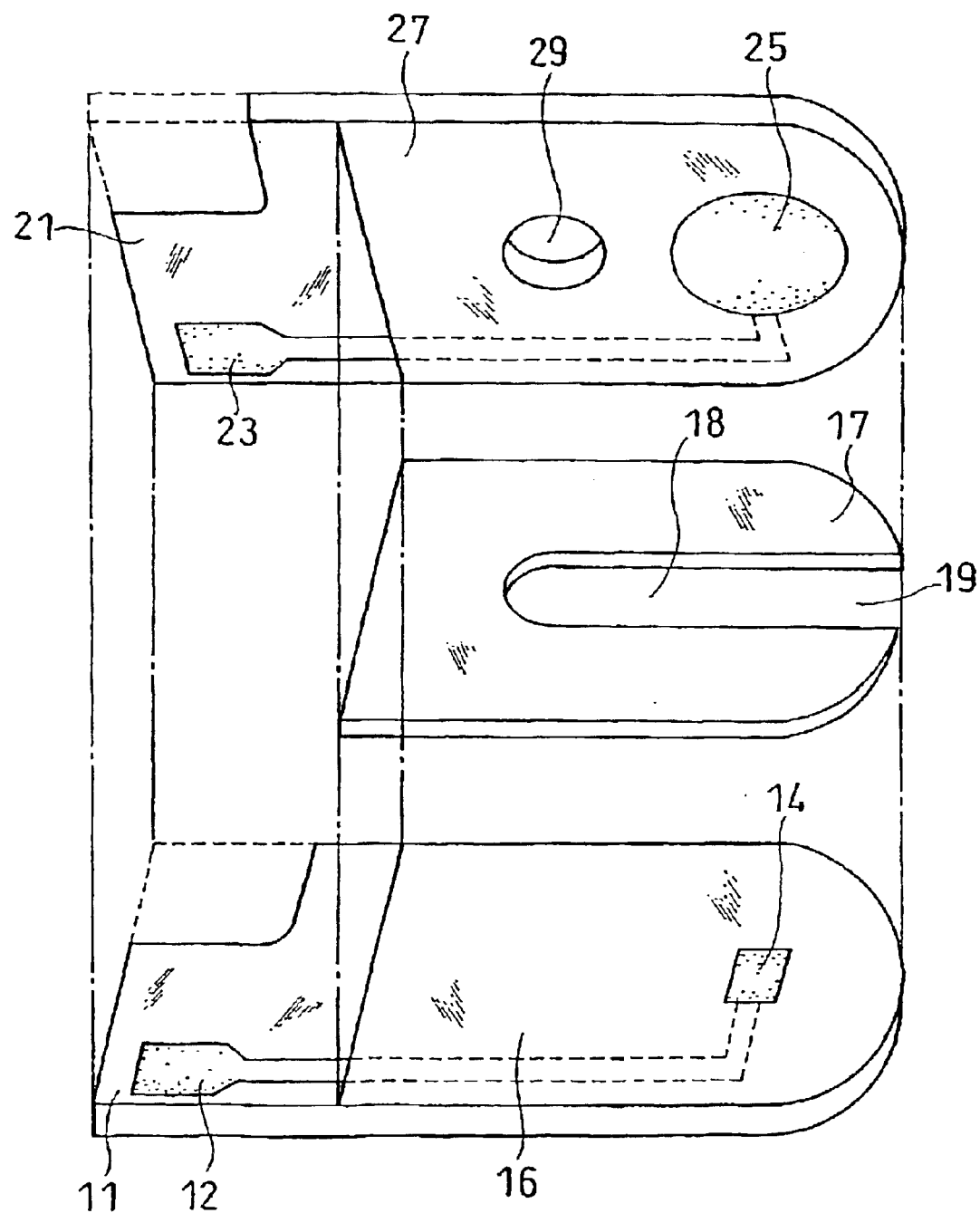
FIG. 1 is an exploded perspective view of a glucose sensor in one embodiment of the present invention from which the reagent layer and surfactant layer are omitted.

As described above, a biosensor of the present invention comprises a first insulating base plate having a working electrode, a second insulating base plate having a counter electrode opposed to the working electrode, a reagent layer comprising at least an oxidoreductase, and a sample supply pathway formed between the first and second insulating base plates, wherein the working electrode, counter electrode and reagent layer are exposed to an inside of the sample supply pathway, and the distance between the working electrode and the counter electrode is 150 μm or less. The distance between the working electrode and the counter electrode is preferably 40 to 150 μm and more preferably 40 to 100 μm.

In the biosensor of the present invention, the amount of a sample solution to be introduced into the sample supply pathway by capillary action is preferably 10 nl to 5 μl and more preferably 50 nl to 500 nl.

This facilitates electric charge transfer between the working electrode and the counter electrode and suppresses spreading of the diffusion layer of an oxidation/reduction species on the working electrode to maintain the concentration gradient of the oxidation/reduction species in the diffusion layer at a high level, thereby increasing the sensor response.

It is preferred that the area $S_2$ of the portion of the counter electrode exposed to the sample supply pathway be equal to or smaller than the area $S_1$ of the portion of the working electrode exposed to the sample supply pathway and that the counter electrode be positioned immediately above the working electrode. The counter electrode being positioned immediately above the working electrode means that the whole counter electrode is positioned so as to overlap the working electrode when viewed from the direction perpendicular to the working electrode.

In measurement systems of the electrochemical field, the area of the counter electrode is generally made to be larger than the area of the working electrode such that the reaction on the counter electrode does not become a rate-determining step. However, in the biosensor of the present invention in which the counter electrode and the working electrode are arranged at opposite positions, when the area of the counter electrode is equal to or smaller than that of the working electrode, the current density on the counter electrode becomes higher than when the area of the counter electrode is larger than that of the working electrode; presumably for this reason or other reasons, the concentration of the oxidation/reduction species in the vicinity of the counter electrode becomes higher. As a result, highly sensitive quantification of a substrate becomes possible since the sensor response is dependent on the concentration of the oxidation/reduction species in the vicinity of the counter electrode. Also, since the reduction in area of the counter electrode enables reduction in volume of the sample supply pathway, reduction in the amount of sample becomes possible. The area of the counter electrode is preferably smaller than that of the working electrode. This makes the above-described effects more remarkable.

It is preferable to form the working electrode on the first insulating base plate and form the counter electrode on the second insulating base plate. This facilitates the manufacturing process of the biosensor.

The first base plate and the second base plate are preferably configured so as to sandwich a spacer member. This increases the strength against physical pressure applied to the base plates, thereby enabling prevention of short-circuit caused by the contact between the working electrode and the counter electrode and reduction of the influence of the physical pressure on the current response.

As the first and second base plates of the present invention, it is possible to use any electrically insulating material having sufficient rigidity during storage and measurement. Such examples include thermoplastic resins, such as polyethylene, polystyrene, poly vinyl chloride, polyamide and saturated polyester resin, or thermosetting resins, such as urea resin, melamine resin, phenol resin, epoxy resin and unsaturated polyester resin. Among them, polyethylene terephthalate is preferable in terms of the adhesion to the electrode.

As the spacer member, it is possible to use any electrically insulating material having sufficient rigidity during storage and measurement. Such examples include thermoplastic resins, such as polyethylene, polystyrene, poly vinyl chloride, polyamide and saturated polyester resin, or thermosetting resins, such as urea resin, melamine resin, phenol resin, epoxy resin and unsaturated polyester resin.

As the working electrode, it is possible to use any conductive material which is not subject to oxidation upon oxidation of the electron mediator. As the counter electrode, it is possible to use any commonly used conductive material such as palladium, gold, platinum or carbon.

As the oxidorecuctase, one adequate for the substrate contained in the sample to be measured may be used. Such examples include fructose dehydrogenase, glucose oxidase, glucose dehydrogenase, alcohol oxidase, lactate oxidase, cholesterol oxidase, xanthine oxidase, amino acid oxidase, etc.

The biosensor of the present invention preferably comprises an electron mediator in the reagent layer. Examples of the electron mediator include potassium ferricyanide, p-benzoquinone, phenazine methosulfate, methylene blue, and ferrocene derivatives. Also, even when oxygen is used as the electron mediator, current response is obtained. These electron mediators are used singly or in combination of two or more.

The biosensor of the present invention preferably comprises a hydrophilic polymer in the reagent layer. Various hydrophilic polymers may be used. Such examples include hydroxyethyl cellulose, hydroxypropyl cellulose, methyl cellulose, ethyl cellulose, ethylhydroxyethyl cellulose, carboxymethyl cellulose, polyvinyl pyrrolidone, polyvinyl alcohol, polyamino acid such as polylysine, polystyrene sulfonate, gelatin and its derivatives, polyacrylic acid and its salts, plolymethacrylic acid and its salts, starch and its derivatives, and a polymer of maleic anhydride or its salt. Among them, carboxymethyl cellulose, hydroxyethyl cellulose and hydroxypropyl cellulose are particularly preferred.

In the following, embodiments of the present invention will be described with reference to drawings. In drawings showing the structure, positional relationship and size of respective elements are not necessarily accurate.

Embodiment 1

A glucose sensor will be described as an example of the biosensor.

Figure 2:
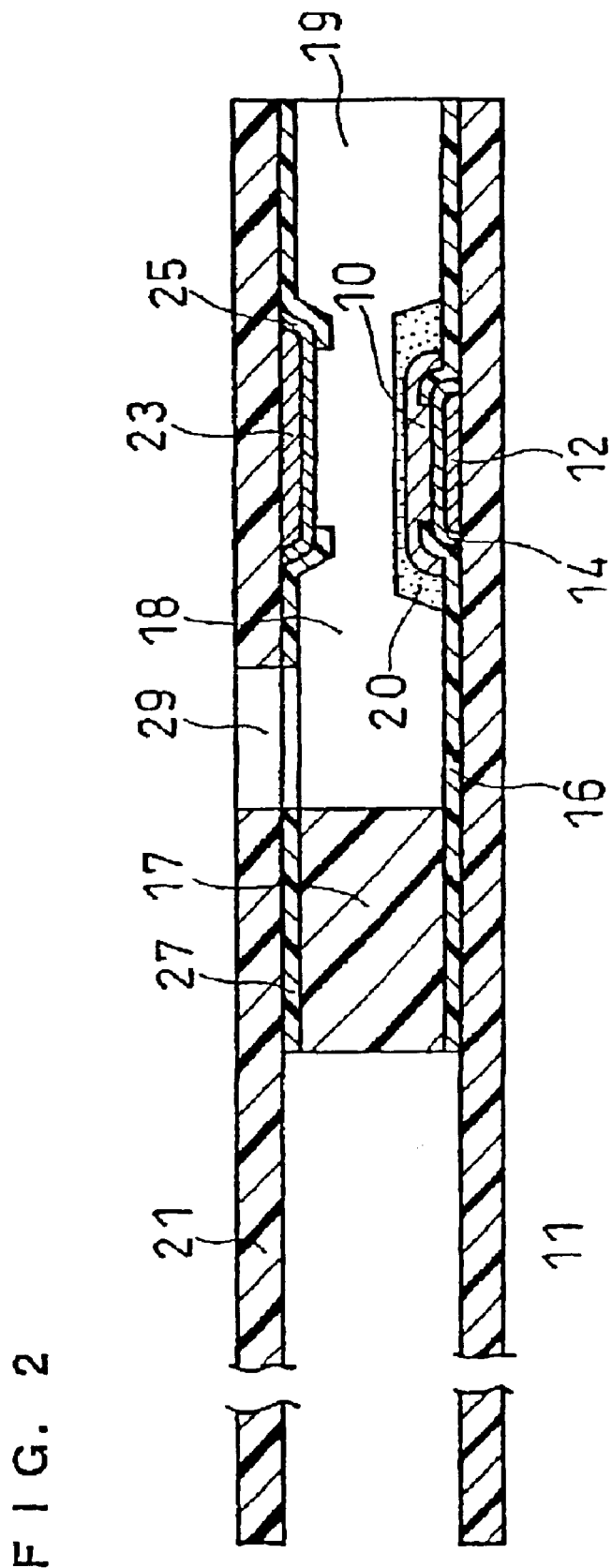
FIG. 2 is a longitudinal cross-sectional view of the same glucose sensor.

With reference to FIG. 1 and FIG. 2, this embodiment will be described. FIG. 1 is an exploded perspective view of a glucose sensor in this embodiment from which the reagent layer and surfactant layer are omitted, and FIG. 2 is a longitudinal cross-sectional view of the glucose sensor.

Numeral 11 denotes a first electrically insulating base plate made of polyethylene terephthalate. A silver paste is printed on the base plate 11 by screen printing to form a working electrode lead 12 and an electrode base, and a conductive carbon paste containing a resin binder is subsequently printed on the electrode base to form a working electrode 14. The working electrode 14 is in contact with the working electrode lead 12. Further, an insulating paste is printed on the base plate 11 to form an insulating layer 16. The insulating layer 16 covers the outer periphery of the working electrode 14 so as to keep the exposed area of the working electrode 14 constant.

Thereafter, a silver paste is printed on the back side of a second electrically insulating base plate 21 to form a counter electrode lead 23 and an electrode base, a conductive carbon paste is subsequently printed on the electrode base to form a counter electrode 25, and an insulating paste is printed to form an insulating layer 27 such that the exposed area of the counter electrode 25 becomes larger than the exposed area of the working electrode 14. The base plate 21 is provided with an air vent 29.

An aqueous solution containing GOD as an enzyme and potassium ferricyanide as an electron mediator is dropped over the working electrode 14 on the base plate 11 and is then dried to form a reagent layer 10. Over the reagent layer 10 is further formed a surfactant layer 20 containing lecithin as a surfactant.

Finally, the base plate 11, the base plate 21 and a spacer member 17 are bonded to one another in a positional relationship as shown by the dashed lines in FIG. 1, which gives a glucose sensor as shown in FIG. 2.

The spacer member 17 to be interposed between the base plate 11 and the base plate 21 has a slit 18, and the slit 18 forms a space serving as a sample supply pathway between the base plates 11 and 21. By varying the thickness of the spacer member 17, the height of the sample supply pathway, i.e., the distance between the working electrode 14 and the counter electrode 25 can be varied.

An air vent 29 of the base plate 21 communicates with the sample supply pathway; thus, when a sample is brought in contact with a sample supply port 19 formed at an open end of the slit 18, the sample readily reaches the reagent layer 10 in the sample supply pathway by capillary action.

Embodiment 2

Figure 3:
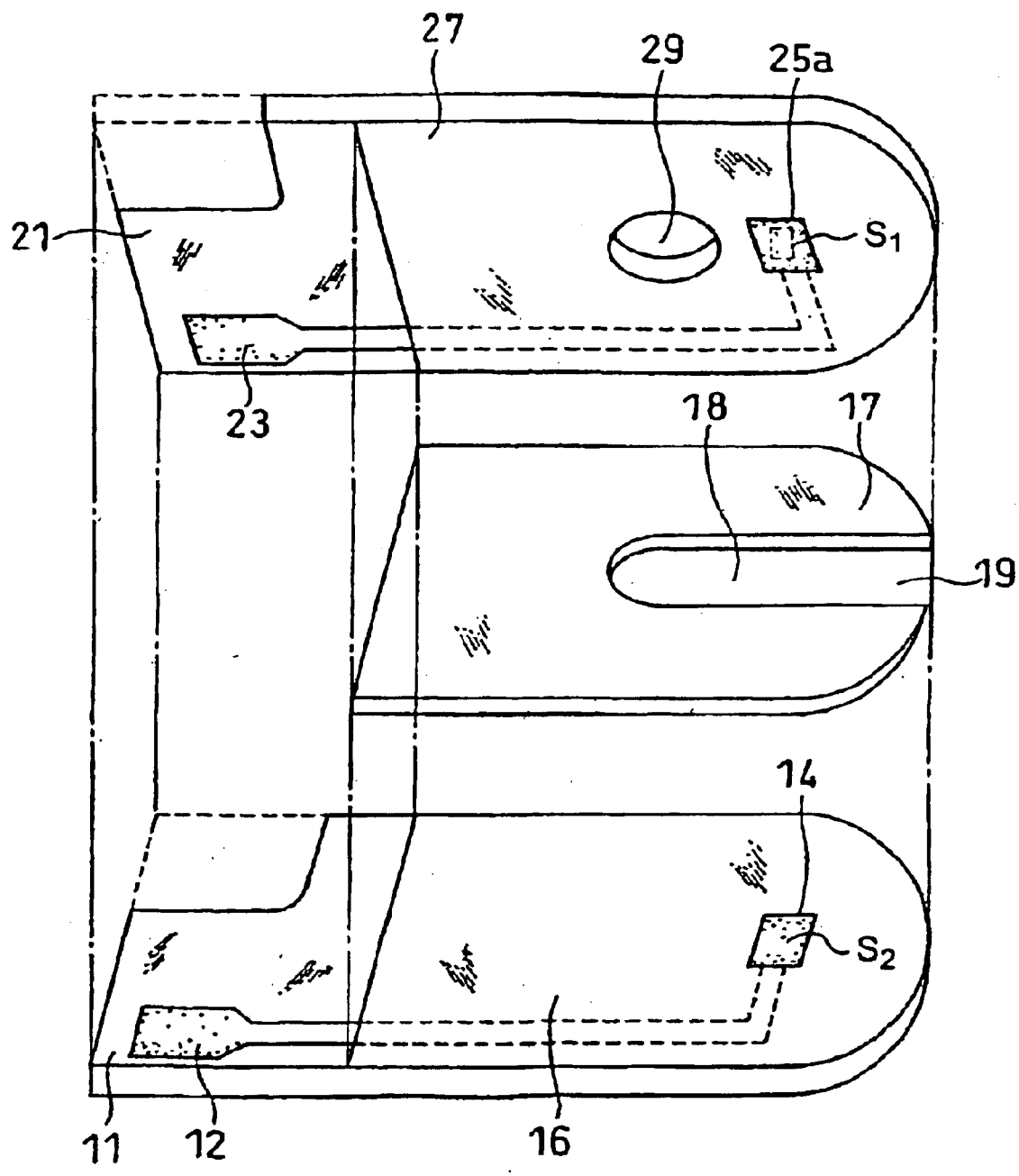
FIG. 3 is an exploded perspective view of a glucose sensor in another embodiment of the present invention from which the reagent layer and surfactant layer are omitted.

FIG. 3 is a perspective view of a glucose sensor in this embodiment from which the reagent layer and the surfactant layer are omitted. In this embodiment, a counter electrode 25a is a rectangle similar to that of working electrode 14. The area ($S_1$) of counter electrode 25a is the same as (solid line) or less than (broken line) that of the working electrode ($S_2$). Other than these, this embodiment is the same as Embodiment 1.

Embodiment 3

Figure 4:
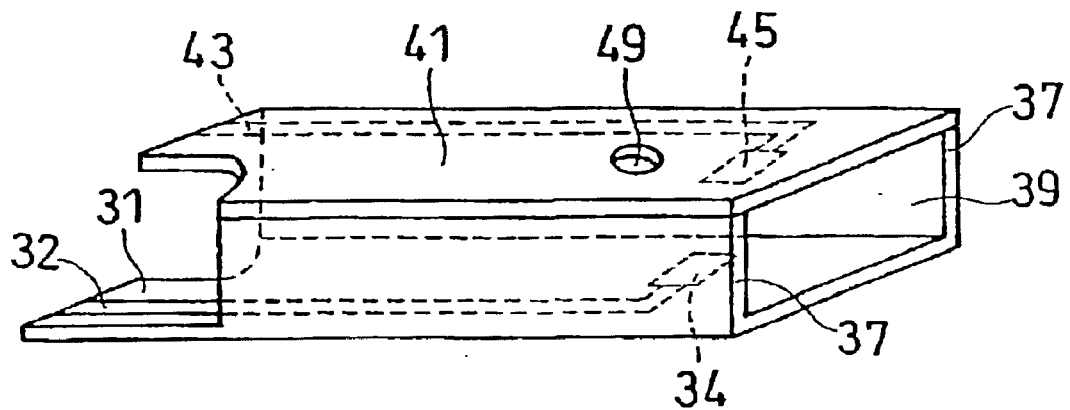
FIG. 4 is an exploded perspective view of a glucose sensor in still another embodiment of the present invention from which the reagent layer and surfactant layer are omitted.
Figure 5:
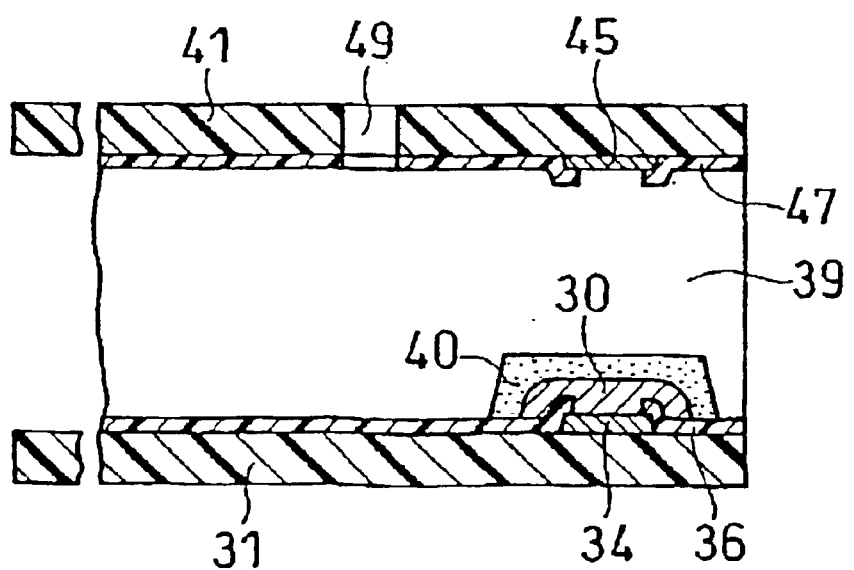
FIG. 5 is a longitudinal cross-sectional view of the same glucose sensor.

FIG. 4 is a perspective view of a glucose sensor in this embodiment from which the reagent layer and surfactant layer are omitted, and FIG. 5 is a longitudinal cross-sectional view of the glucose sensor.

This glucose sensor is produced in the following procedure.

Palladium is sputtered on an electrically insulating base plate 31 having upright pieces 37, 37 at both sides, to form a working electrode 34 and its lead 32. Next, an insulating member 36 is attached to the base plate 31 to define the working electrode 34 and a terminal portion of the lead 32 to be inserted into a measuring device. Similarly, palladium is sputtered on the inner side of a second electrically insulating base plate 41 to form a counter electrode 45 and its lead 43. Subsequently, an insulating member 47 is attached to the inner side of the base plate 41 to define the counter electrode 45 and a terminal portion of the lead 43 to be inserted into the measuring device.

Thereafter, the second base plate is joined to the base plate 31. Then, the working electrode 34 and the counter electrode 45 are arranged at opposite positions of a space formed between the base plate 31 and the base plate 41. The distance between the working electrode and the counter electrode is, for example, 100 $\mu$m. A reagent layer 30 and a surfactant layer 40 are formed so as to cover the electrode 34 in the same manner as in Embodiment 1. In a sensor thus produced, the end face closer to the electrodes 34 and 45 serves as a sample supply port 39. A sample supplied from this port reaches the electrode portion by capillary action of the space communicating with an air vent 49.

Embodiment 4

Figure 6:
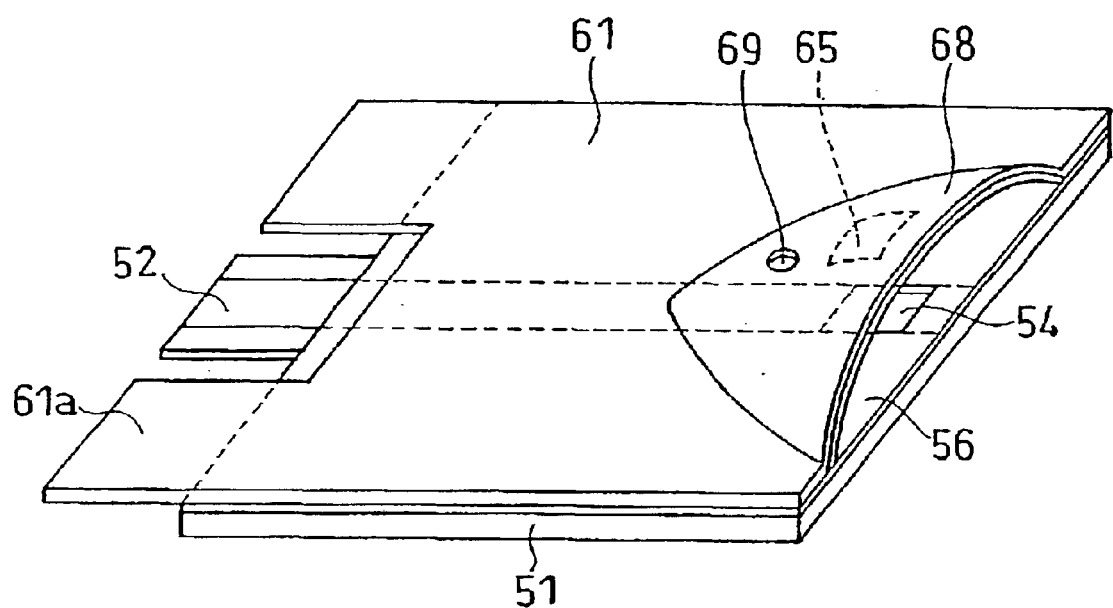
FIG. 6 is an exploded perspective view of a glucose sensor in still another embodiment of the present invention from which the reagent layer and surfactant layer are omitted.
Figure 7:
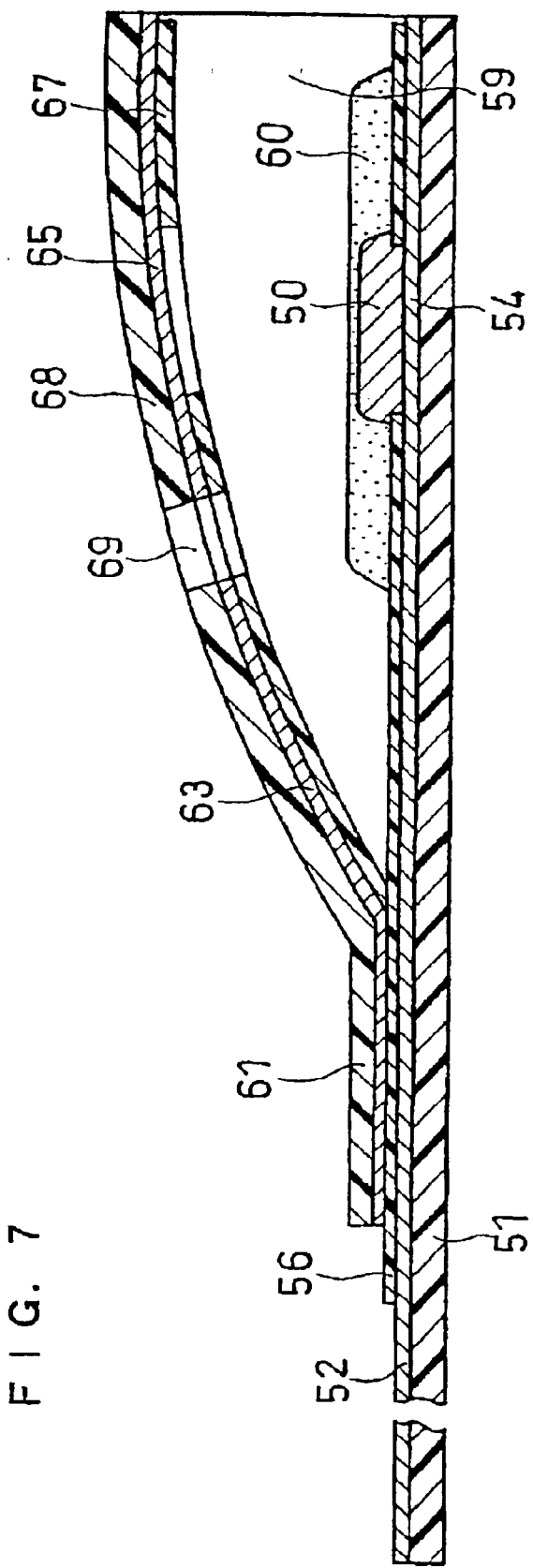
FIG. 7 is a longitudinal cross-sectional view of the same glucose sensor.

FIG. 6 is a perspective view of a glucose sensor in this embodiment from which the reagent layer and surfactant layer are omitted, and FIG. 7 is a longitudinal cross-sectional view of the glucose sensor.

This glucose sensor is produced in the following procedure.

Palladium is sputtered on a first electrically insulating base plate 51 to form a working electrode 54 and its lead 52. Next, an insulating member 56 is attached to the base plate 51 to define the working electrode 54 and a terminal portion of the lead 52 to be inserted into a measuring device. Also, a second electrically insulating base plate 61 has an outwardly expanded curved part 68, and palladium is sputtered on the inner wall of the curved part 68 to form a counter electrode 65 and its lead 63. By adjusting the curvature of the curved part 68, the distance between the working electrode 54 and the counter electrode 65 can be controlled.

Thereafter, an insulating member 67 is attached to the inner wall of the base plate 61 to define the counter electrode 65 and a terminal portion to be inserted into the measuring device. At this time, the area of the counter electrode 65 is made to be equal to that of the working electrode 54. The terminal portion of the counter electrode 65 is exposed to the back side of a rear end 61a of the base plate 61. The curved part 68 has an air vent 69 at its end. A reagent layer 50 is formed on the working electrode 54, and a surfactant layer 60 is further formed so as to cover the reagent layer 50. Lastly, the base plate 51 and the base plate 61 are bonded to fabricate a glucose sensor.

EXAMPLE 1

Five kinds of sensors having a different-height sample supply pathway were produced by varying the thickness of the spacer member 17 in Embodiment 1. The area of the working electrode is 1.0 mm². The counter electrode is a circle having a diameter of about 3.6 mm, and since this diameter is greater than the width of the slit 18 of the spacer member 17, part of the counter electrode is not exposed to the sample supply pathway. The area of the portion of the counter electrode exposed to the sample supply pathway is about 5.3 mm².

Figure 8:
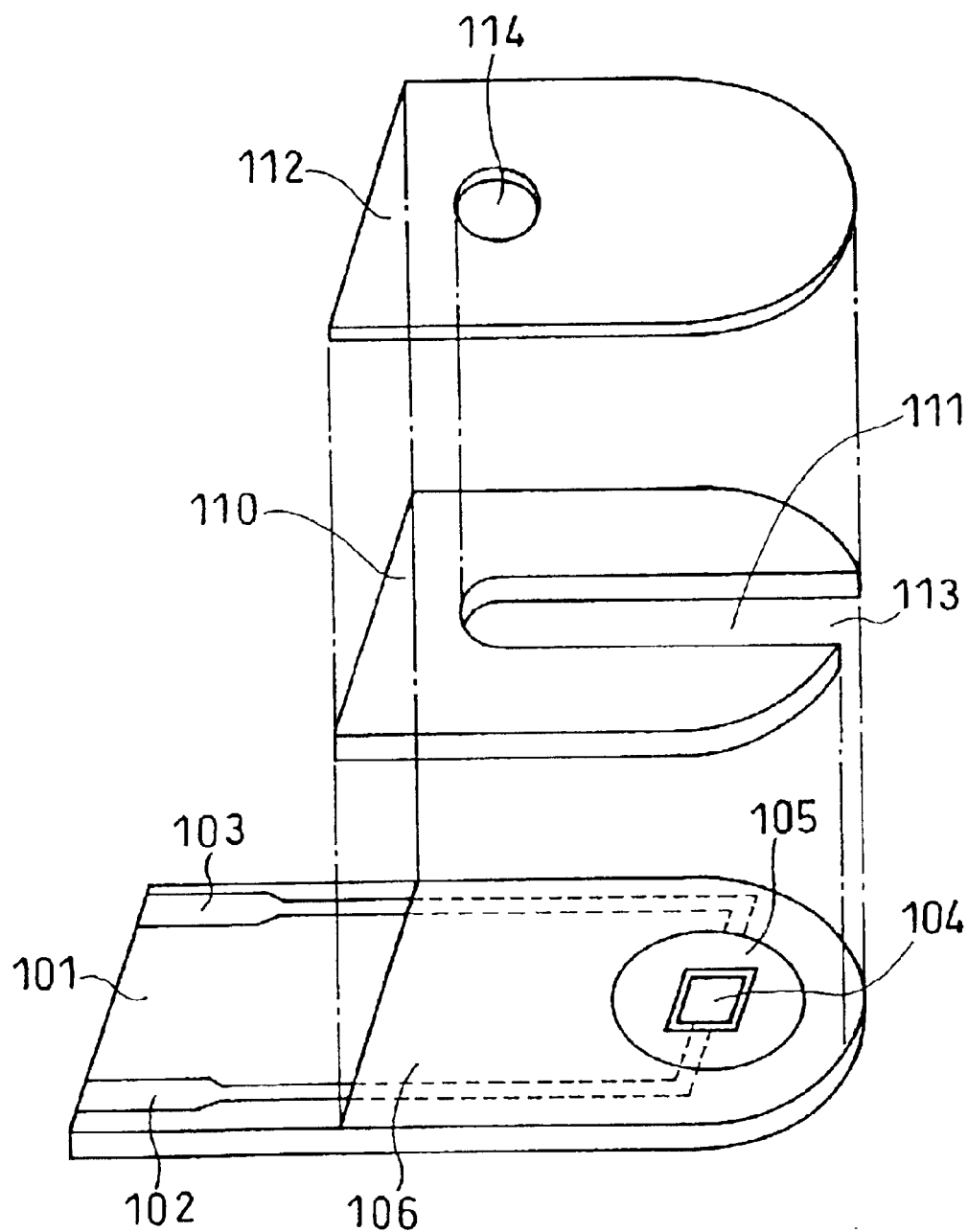
FIG. 8 is an exploded perspective view of a glucose sensor in a comparative example from which the reagent layer and surfactant layer are omitted.
Figure 9:
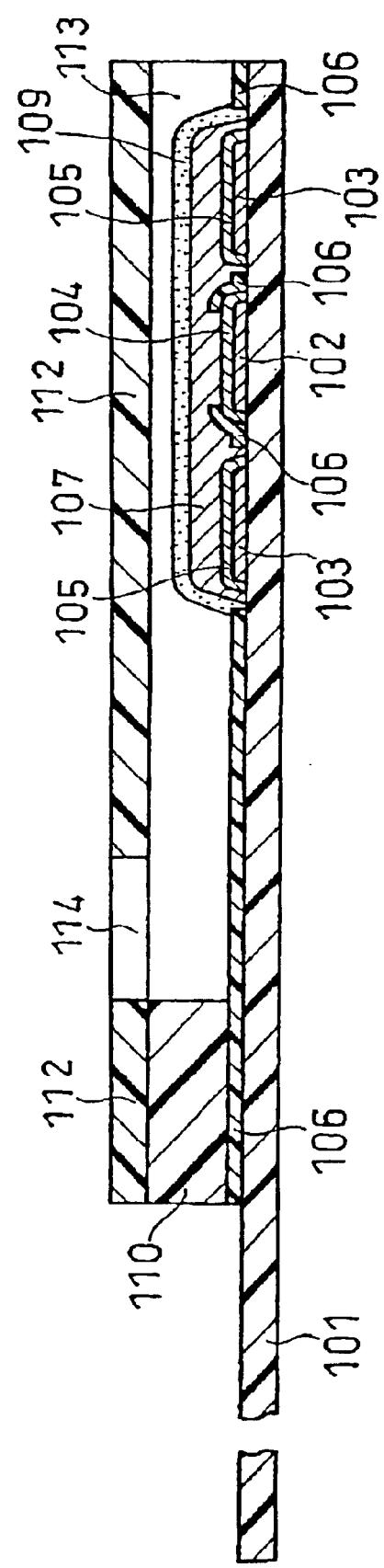
FIG. 9 is a longitudinal cross-sectional view of the same glucose sensor.

As a comparative example, glucose sensors having a working electrode and a counter electrode formed on the same base plate were produced. In the same manner as in Example 1, five kinds of glucose sensors having a different-height sample supply pathway were produced. FIG. 8 is a decomposed perspective view of a sensor of the comparative example from which the reagent layer and surfactant layer are omitted, and FIG. 9 is a longitudinal cross-sectional view of the sensor.

A silver paste was printed on an electrically insulating base plate 101 made of polyethylene terephthalate by screen printing to form a working electrode lead 102 and a counter electrode lead 103. Then, a conductive carbon paste containing a resin binder was printed to form a working electrode 104. The working electrode 104 is in contact with the working electrode lead 102. Further, an insulating paste was printed on the base plate 101 to form an insulating layer 106. The insulating layer 106 covers the outer periphery of the working electrode 104 so as to keep the exposed area of the working electrode 104 constant. Thereafter, a conductive carbon paste containing a resin binder was printed on the base plate 101 so as to be in contact with the counter electrode lead 103, thereby to form a counter electrode 105. The area of the working electrode 104 is 1.0 mm², and the area of the portion of the counter electrode 105 exposed to the sample supply pathway is about 4.3 mm².

An aqueous solution containing GOD as the enzyme and potassium ferricyanide as the electron mediator was dropped over the working electrode 104 and the counter electrode 105 and was then dried to form a reagent layer 107, and a surfactant layer 109 containing lecithin as the surfactant was further formed over the reagent layer 107. The base plate 101, a cover 112 having an air vent 114, and a spacer member 110 having a slit 111 were bonded to one another in a positional relationship as shown by the dashed lines in FIG. 8.

Using the above-described sensors of Example 1 and the comparative example, measurements were performed for the glucose concentration of aqueous solutions containing certain amounts of glucose. A sample was supplied from the sample supply port to the sample supply pathway, and after a lapse of certain time, a voltage of 500 mV was applied to the working electrode with respect to the counter electrode. Upon the voltage application, the value of a current flowing between the working electrode and the counter electrode was detected, and the current response observed was proportional to the glucose concentration of the sample.

Figure 10:
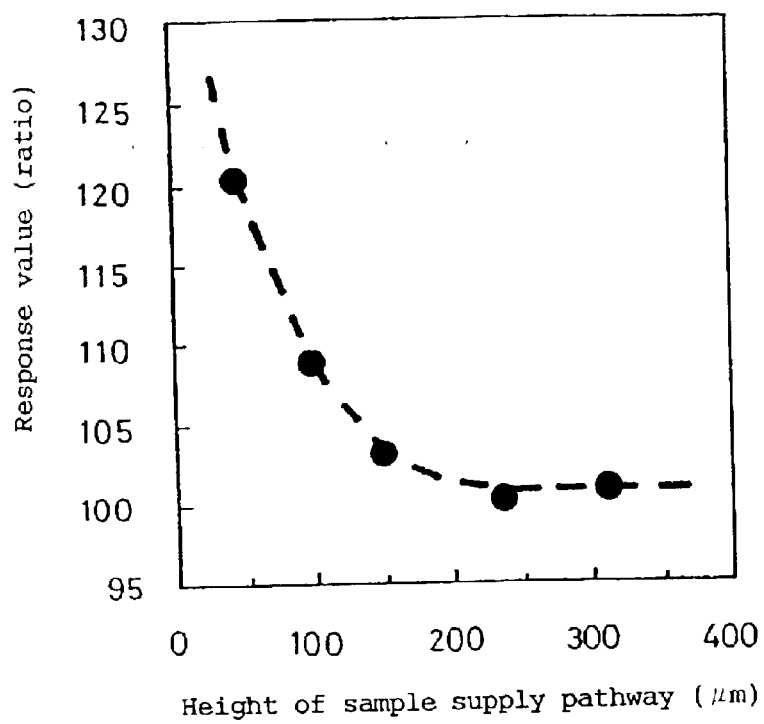
FIG. 10 is a graph showing the relationship between the response current value (ratio) and the height of sample supply pathway in glucose sensors of Example 1 of the present invention.

Using solutions containing glucose at 180 mg/dl and the respective glucose sensors having a different-height sample supply pathway, the value of response current was measured. FIG. 10 shows the relationship between the height of the sample supply pathway and the response value (ratio) in the sensors of Example 1. The response value (ratio) is expressed in a ratio obtained by defining the response value of the sensor of the comparative example of which sample supply pathway has the same height as 100.

As shown by FIG. 10, the response value (ratio) of Example 1 relative to the comparative example sharply increases when the height of the sample supply pathway is 150 μm or less. The reason may be as follows: when the working electrode and the counter electrode are opposed to each other with the distance between the working electrode and the counter electrode being 150 μm or less, growth of the diffusion layer of the oxidation/reduction species on the working electrode is suppressed so that the concentration of the oxidation/reduction species on the counter electrode is reflected in the sensor response, and electric charge transfer between the working electrode and the counter electrode or the like becomes favorable.

In Example 1, the amount of sample necessary for measurement was about 0.5 to 3.0 μl. In this way, according to the present invention, since the distance between the working electrode and the counter electrode is limited, it is possible to reduce the amount of sample necessary for measurement.

EXAMPLE 2

Figure 11:
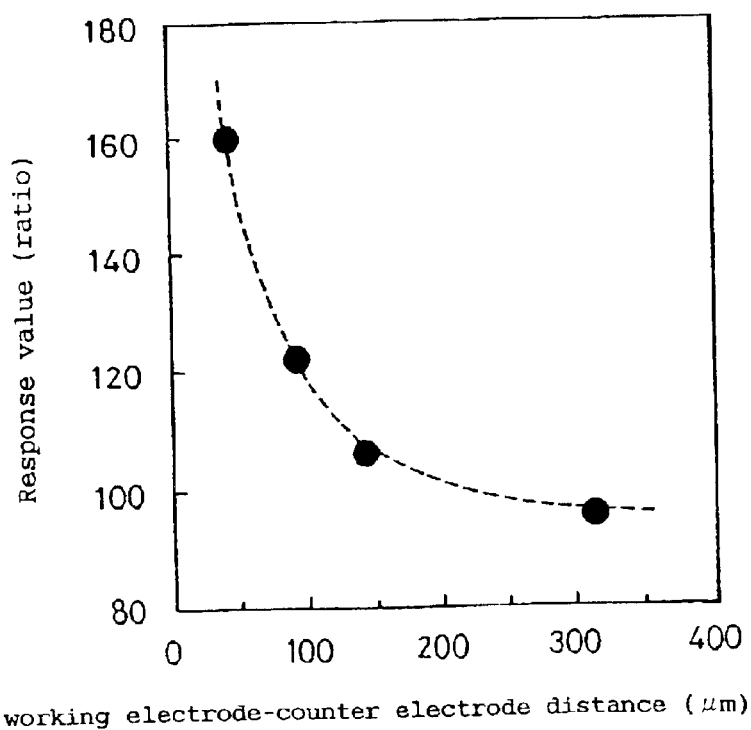
FIG. 11 is a graph showing the relationship between the response current value (ratio) and the distance between the working electrode and the counter electrode in glucose sensors of Example 2 of the present invention.

Biosensors were produced in the same manner as in Example 1 except that the areas of both the working electrode and the counter electrode were made 1.0 mm² in Embodiment 2. Then, using solutions containing glucose at 90 mg/dl and the respective glucose sensors having a different-height sample supply pathway, the value of response current was measured. FIG. 11 shows the relationship between the height of the sample supply pathway, i.e., the distance between the working electrode and the counter electrode, and the response value (ratio) in the sensors of Example 2. The response value (ratio) is expressed in a ratio obtained by defining the response value of the sensor of Example 1 of which sample supply pathway has the same height as 100.

As shown by FIG. 11, the response value (ratio) of the sensors of Example 2 relative to Example 1 sharply increases when the height of the sample supply pathway is 150 μm or less. The reason may be as follows: when the working electrode and the counter electrode are opposed to each other with the distance between the working electrode and the counter electrode being 150 μm or less, growth of the diffusion layer of the oxidation/reduction species on the working electrode is suppressed so that the concentration of the oxidation/reduction species on the counter electrode is reflected in the sensor response, and electric charge transfer between the working electrode and the counter electrode or the like becomes favorable.

In general electrochemical systems, the area of the counter electrode is made larger than that of the working electrode in order to prevent the reaction on the counter electrode from becoming a rate-determining step. However, in this system, since the working electrode and the counter electrode are arranged at opposite positions, the current density on the counter electrode is reflected in the current response; presumably for this reason or other reasons, it was possible to obtain high response current in comparison with the case where the area of the counter electrode was larger than that of the working electrode.

In this example, since the area of the counter electrode is equal to that of the working electrode, the position of the air vent 29 is made closer to the sample supply port side than in Example 1. Thus, it becomes possible to further reduce the amount of sample necessary for measurement.

EXAMPLE 3

Figure 12:
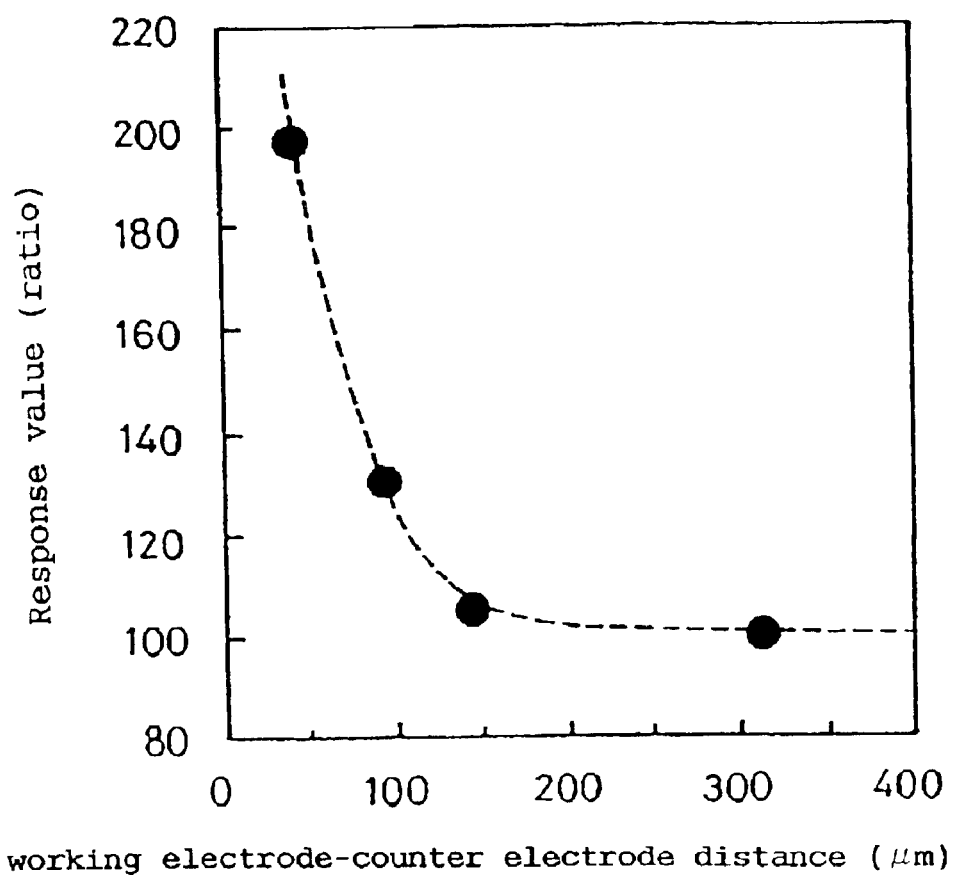
FIG. 12 is a graph showing the relationship between the response current value (ratio) and the distance between the working electrode and the counter electrode in glucose sensors of Example 3 of the present invention.

In this example, biosensors were produced in the same manner as in Example 2 except that the area of the counter electrode was made 0.64 mm². Using solutions containing glucose at 90 mg/dl and the respective glucose sensors having a different-height sample supply pathway, the value of response current was measured. FIG. 12 shows the relationship between the height of the sample supply pathway (the distance between the working electrode and the counter electrode) and the response value (ratio) in the sensors of Example 3. The response value (ratio) is expressed in a ratio obtained by defining the response value of the sensor of Example 1 of which sample supply pathway has the same height as 100.

As shown by FIG. 12, the response value (ratio) of this example relative to Example 1 sharply increases when the distance between the working electrode and the counter electrode is 150 μm or less. This is presumably because of the same reasons as those of Example 2.

In this example, since the area of the counter electrode is smaller than that of the working electrode, the position of the air vent can be made closer to the sample supply port side than in Example 2. Thus, it becomes possible to further reduce the amount of sample necessary for measurement than in Example 2.

Industrial Applicability

As described above, according to the present invention, it is possible to obtain a highly sensitive biosensor that needs a smaller amount of sample for measurement.

What is claimed is:

1. A biosensor comprising a first insulating base plate having a working electrode, a second insulating base plate having a counter electrode opposed to said working electrode, a reagent layer comprising at least an oxidoreductase, and a sample supply pathway formed between the first and second insulating base plates, wherein said working electrode, counter electrode and reagent layer are exposed to an inside of said sample supply pathway, and the distance between said working electrode and said counter electrode is 150 μm or less, and the area of said counter electrode exposed to the sample supply pathway is smaller than the area of said working electrode exposed to the sample supply pathway.

2. The biosensor in accordance with claim 1, wherein the area of said working electrode exposed to the sample supply pathway is 0.1 to 2.0 mm², and the area of said counter electrode exposed to the sample supply pathway is in a range of not less than 0.05 mm² and less than 2.0 mm².

3. The biosensor in accordance with claim 1, wherein the distance between said working electrode and said counter electrode is 40 μm or more.

4. The biosensor in accordance with claim 1, wherein a spacer member having a slit is interposed between the first and second insulating base plates such that said sample supply pathway is formed in said slit.

5. A biosensor comprising a first insulating base plate having a working electrode, a second insulating base plate having a counter electrode opposed to said working electrode, a reagent layer comprising at least an oxidoreductase, and a sample supply pathway formed between the first and second insulating base plates, wherein said working electrode, counter electrode and reagent layer are exposed to said sample supply pathway, and the area of said counter electrode exposed to the sample supply pathway is less than the area of said working electrode exposed to the sample supply pathway.

6. The biosensor in accordance with claim 5, wherein the distance between said working electrode and said counter electrode is 150 μm or less.

* * * * *